US012611177B2

(12) United States Patent
Yen

(10) Patent No.: US 12,611,177 B2
(45) Date of Patent: Apr. 28, 2026

(54) MULTI-BOUNDARY ARRAY ULTRASOUND IMAGING

(71) Applicant: UNIVERSITY OF SOUTHERN CALIFORNIA, Los Angeles, CA (US)

(72) Inventor: Jesse Yen, La Crescenta, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 94 days.

(21) Appl. No.: 18/125,634

(22) Filed: Mar. 23, 2023

(65) Prior Publication Data

US 2023/0301628 A1 Sep. 28, 2023

Related U.S. Application Data

(60) Provisional application No. 63/323,043, filed on Mar. 23, 2022.

(51) Int. Cl.
*A61B 8/00* (2006.01)
*G06T 12/00* (2026.01)

(52) U.S. Cl.
CPC .......... *A61B 8/4477* (2013.01); *A61B 8/4411* (2013.01); *A61B 8/4483* (2013.01); *A61B 8/5207* (2013.01); *G06T 12/00* (2026.01); *G06T 2207/10136* (2013.01)

(58) Field of Classification Search
CPC ... A61B 8/4477; A61B 8/4411; A61B 8/4483; A61B 8/5207; G06T 11/003; G06T 2207/10136
See application file for complete search history.

(56) References Cited

U.S. PATENT DOCUMENTS

| | | | | |
|---|---|---|---|---|
| 2011/0044903 A1* | 2/2011 | Borrelli | ..................... | A61P 7/04 |
| | | | | 424/9.1 |
| 2012/0267986 A1* | 10/2012 | Galluzzo | ............... | B06B 1/0603 |
| | | | | 310/348 |
| 2017/0136265 A1* | 5/2017 | Hyde | ........................ | A61N 7/00 |
| 2019/0343492 A1* | 11/2019 | Miyazawa | ........... | A61B 8/4427 |
| 2021/0346725 A1* | 11/2021 | Rousso | .................. | A61B 8/085 |
| 2022/0331613 A1* | 10/2022 | Sullivan | ................... | A61N 7/00 |

\* cited by examiner

*Primary Examiner* — Dixomara Vargas
(74) *Attorney, Agent, or Firm* — Snell & Wilmer LLP

(57) ABSTRACT

An imaging system may comprise a first rectangular boundary array of a first plurality of ultrasonic transducers, a second rectangular boundary array of a second plurality of ultrasonic transducers positioned within the first rectangular boundary array, and a controller coupled to the first rectangular boundary array and the second rectangular boundary array. A method for image reconstruction may comprise determining whether to deliver energy to a first rectangular boundary array of a first plurality of ultrasonic transducers, or a second rectangular boundary array of a second plurality of ultrasonic transducers, the second rectangular boundary array being positioned within the first rectangular boundary array. The method may comprise determining an amount of energy to be delivered to the first plurality of ultrasonic transducers or the second plurality of ultrasonic transducers, and delivering the amount of energy to the first plurality of ultrasonic transducers or the second plurality of ultrasonic transducers.

11 Claims, 5 Drawing Sheets

100

= Transmit Element

= Receive Element

201

221r

221

211

221t

222r

222t

212

222

201

221r

221

211

221t

222t

212

222

222r

= Low-frequency transmit Element

= Low-frequency receive Element

= High-frequency transmit Element

= High-frequency receive Element

= 1.20 MHz

= 1.85 MHz

= 2.50 MHz

= 3.85 MHz

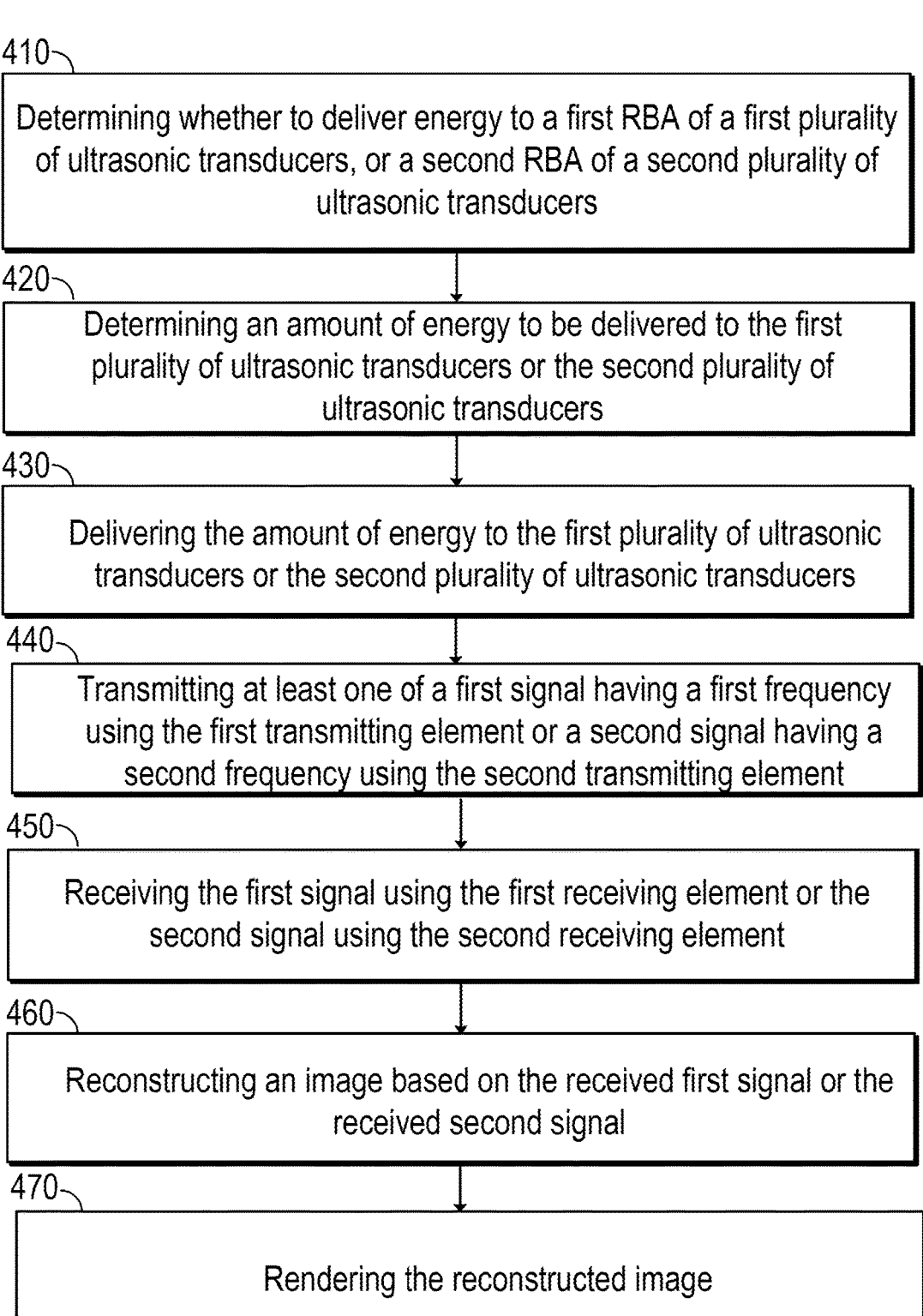

400

410

Determining whether to deliver energy to a first RBA of a first plurality of ultrasonic transducers, or a second RBA of a second plurality of ultrasonic transducers

420

Determining an amount of energy to be delivered to the first plurality of ultrasonic transducers or the second plurality of ultrasonic transducers

430

Delivering the amount of energy to the first plurality of ultrasonic transducers or the second plurality of ultrasonic transducers

440

Transmitting at least one of a first signal having a first frequency using the first transmitting element or a second signal having a second frequency using the second transmitting element

450

Receiving the first signal using the first receiving element or the second signal using the second receiving element

460

Reconstructing an image based on the received first signal or the received second signal

470

Rendering the reconstructed image

FIG. 4

MULTI-BOUNDARY ARRAY ULTRASOUND IMAGING

CROSS-REFERENCE TO RELATED APPLICATIONS

This application claims priority to, and the benefit of, U.S. Prov. Pat. Appl., Ser. No. 63/323,043, entitled "MULTI-BOUNDARY ARRAY ULTRASOUND IMAGING," filed on Mar. 23, 2022, the entirety of which is incorporated herein for all purposes by this reference.

FIELD

The present application relates to the field of ultrasound imaging through improved ultrasonic imaging systems.

BACKGROUND

Ultrasound imaging systems are very useful for creating images of internal structures, such as organs, tissues, and the like, within a body or within other objects, using sound waves. The use of ultrasound imaging systems is useful in the medical field for diagnosis, treatment and other uses to improve health. Moreover, ultrasound imaging systems have many uses in other fields of endeavor. It is desirable to have ultrasound imaging systems that are less expensive to make, lighter weight, and able to form higher resolution images.

SUMMARY

In an example embodiment, an imaging system is disclosed, comprising: a first rectangular boundary array of a first plurality of ultrasonic transducers; a second rectangular boundary array of a second plurality of ultrasonic transducers positioned within the first rectangular boundary array; and a controller coupled to the first rectangular boundary array and the second rectangular boundary array. The controller configured to: control an amount of energy delivered to the first plurality of ultrasonic transducers or the second plurality of ultrasonic transducers.

In an example embodiment, a method for image reconstruction, is disclosed, the method comprising: determining, by a processor, whether to deliver energy to a first rectangular boundary array of a first plurality of ultrasonic transducers, or a second rectangular boundary array of a second plurality of ultrasonic transducers, the second rectangular boundary array being positioned within the first rectangular boundary array. The method further comprising determining, by the processor, an amount of energy to be delivered to the first plurality of ultrasonic transducers or the second plurality of ultrasonic transducers. The method further comprising delivering, by the processor, the amount of energy to the first plurality of ultrasonic transducers or the second plurality of ultrasonic transducers.

In an example embodiment, a non-transitory computer-readable medium is disclosed, the same comprising computer readable instructions, which when executed by a processor, cause the processor to perform operations comprising: determining, by a processor, whether to deliver energy to a first boundary array of a first plurality of ultrasonic transducers, or a second boundary array of a second plurality of ultrasonic transducers, the second boundary array being positioned within the first boundary array; determining, by the processor, an amount of energy to be delivered to the first plurality of ultrasonic transducers or the second plurality of ultrasonic transducers; and delivering, by the processor, the amount of energy to the first plurality of ultrasonic transducers or the second plurality of ultrasonic transducers.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

FIG. 4 is a bock diagram of an example imaging system method in accordance with various example embodiments.

DETAILED DESCRIPTION

Figure 1:
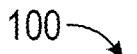
FIG. 1 shows an example block schematic diagram of an imaging system employed to provide imaging using ultrasonic transducers according to an aspect of the invention.
Figure 1:
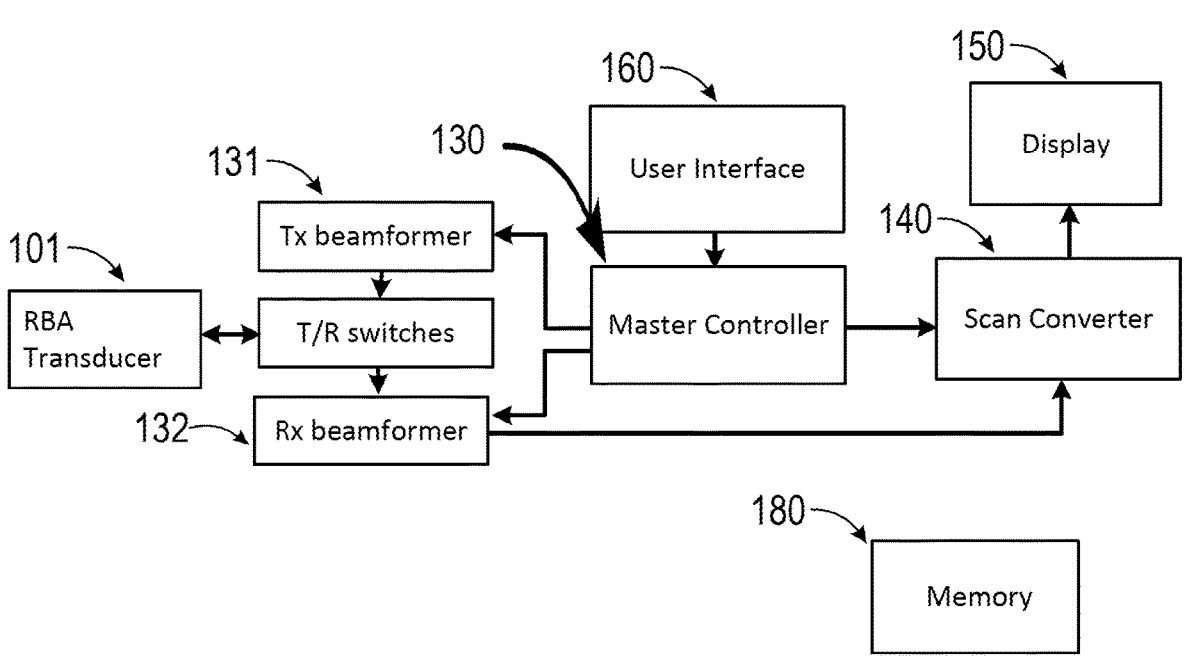

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

In accordance with an example embodiment, a system, apparatus and/or method for an imaging system is disclosed. In accordance with various example embodiments, the imaging system uses ultrasonic transducers arranged in a two-dimensional (2D) or three-dimensional (3D) array to perform 2D or 3D imaging. The imaging system may use a multi-rectangular boundary array that has an outer rectangular boundary array, an inner rectangular boundary array. In another example embodiment, the imaging system may comprise any number of other rectangular or other polygonal-shaped boundary arrays of ultrasonic transducers arranged within each other to perform imaging.

The imaging system may be employed on a patient with a wide-range of conditions, ailments, diseases and/or impairments and/or on different portions of the patient. The imaging system when employing the 2D or 3D array of ultrasonic transducers is capable of real-time 2D and/or 3D ultrasound imaging. In an example embodiment, the imaging system disclosed herein is composed of less transducers and/or other interconnected components than a fully connected array of ultrasonic transducers. When combined with other signal processing and beamforming algorithms and techniques, the quality of the produced 2D or 3D image is comparable to the quality produced by a fully connected array but with significantly less components, and thus, the manufacturing complexity and costs are reduced. Moreover, the 2D or 3D array may be used in advanced imaging techniques, such as dual-frequency imaging and super-resolution imaging. The imaging system provides 2D and 3D images that are comparable and/or better than images produced by a fully connected array of ultrasonic transducers.

In accordance with various example embodiments, and with reference to FIG. 1, an imaging system 100 is disclosed. In an example embodiment, the imaging system 100 may comprise a transducer 101. In an example embodiment, the transducer 101 is a rectangular boundary array ("RBA") transducer. The transducer, in an example embodiment, may comprise a first rectangular boundary array of a first plurality of ultrasonic transducers and a second rectangular boundary array of a second plurality of ultrasonic transducers. In an example embodiment, the second RBA is positioned within the first RBA.

In an example embodiment, the imaging system 100 further comprises a controller 130 coupled to the first RBA and the second RBA. The controller 130 may be configured to control an amount of energy delivered to the first plurality of ultrasonic transducers or the second plurality of ultrasonic transducers. In an example embodiment, the controller may be coupled to a transmit beamformer 131 and a receive beamformer 132, for controlling the transmission and/or reception of signals to/from the transducer 101. In an example embodiment, a transmit/receive switch(es) are configured to switch between passing transmit signals from the transmit beamformer 131 to the transducer 101, on the one hand, and passing receive signals from the transducer 101 to the receive beamformer 132, on the other hand.

In an example embodiment, the imaging system 100 may further comprise a scan converter 140 coupled to the controller 130 and the receive beam former 132, for receiving the receive signals from the receive beamformer 132. The controller 130 may be configured to control the scan converter 140.

The imaging system may include a computing system. One or more of the elements described herein for the computing system may be part of the controller 130, or may be associated with the controller 130. The computing system may include a computing device that has one or more processors, a memory 180 and/or a bus and/or other mechanisms for communicating between the one or more processors. The one or more processors may be implemented as a single processor or as multiple processors. The one or more processors may execute instructions stored in the memory to implement the applications and/or detection of the computing system.

The one or more processors may be coupled to the memory 180. The memory may include one or more of a Random Access Memory (RAM) or other volatile or non-volatile memory. The memory may be a non-transitory memory or a data storage device, such as a hard disk drive, a solid-state disk drive, a hybrid disk drive, or other appropriate data storage, and may further store machine-readable instructions, which may be loaded and executed by the one or more processors.

The memory may include one or more of random access memory ("RAM"), static memory, cache, flash memory and any other suitable type of storage device or computer readable storage medium, which is used for storing instructions to be executed by the one or more processors. The storage device or the computer readable storage medium may be a read only memory ("ROM"), flash memory, and/or memory card, that may be coupled to a bus or other communication mechanism. The storage device may be a mass storage device, such as a magnetic disk, optical disk, and/or flash disk that may be directly or indirectly, temporarily or semi-permanently coupled to the bus or other communication mechanism and used be electrically coupled to some or all of the other components within the computing system including the memory 180, the user interface 160 and/or the communication interface via the bus.

In an example embodiment, the imaging system 100 further comprises a generator, forming part of transmit beamformer 131, coupled to the first plurality of ultrasonic transducers and the second plurality of ultrasonic transducers. The transmit beamformer 131 may be configured to deliver the energy to the first plurality of ultrasonic transducers or the second plurality of ultrasonic transducers.

Figure 2A:
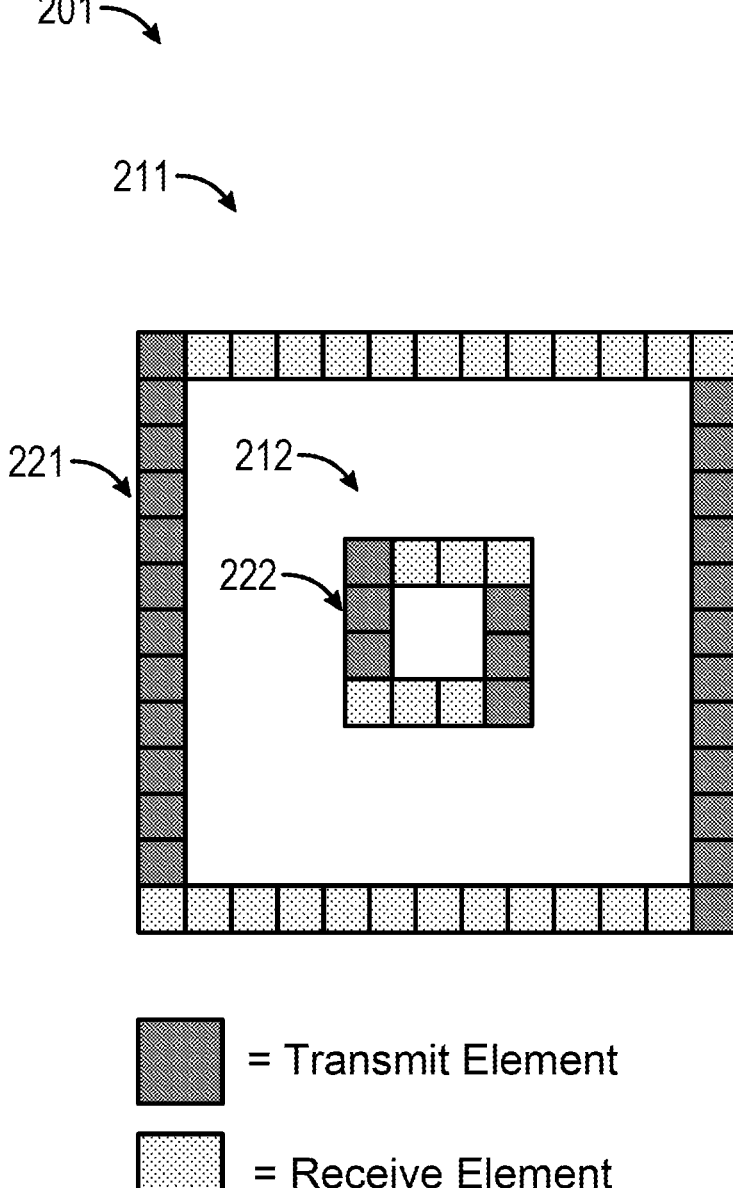
FIGS. 2A-2C are example block diagrams of rectangular boundary array transducers in accordance with various example embodiments.
Figure 2B:
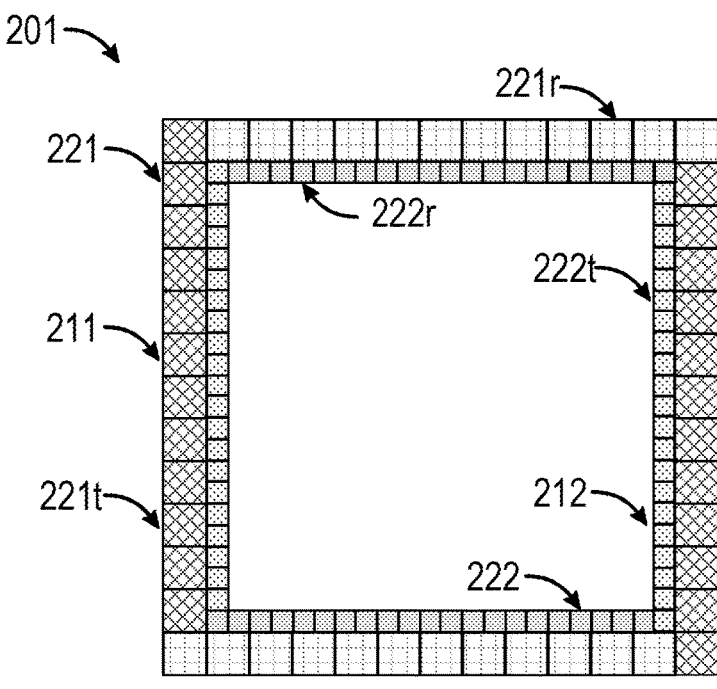
Figure 2C:
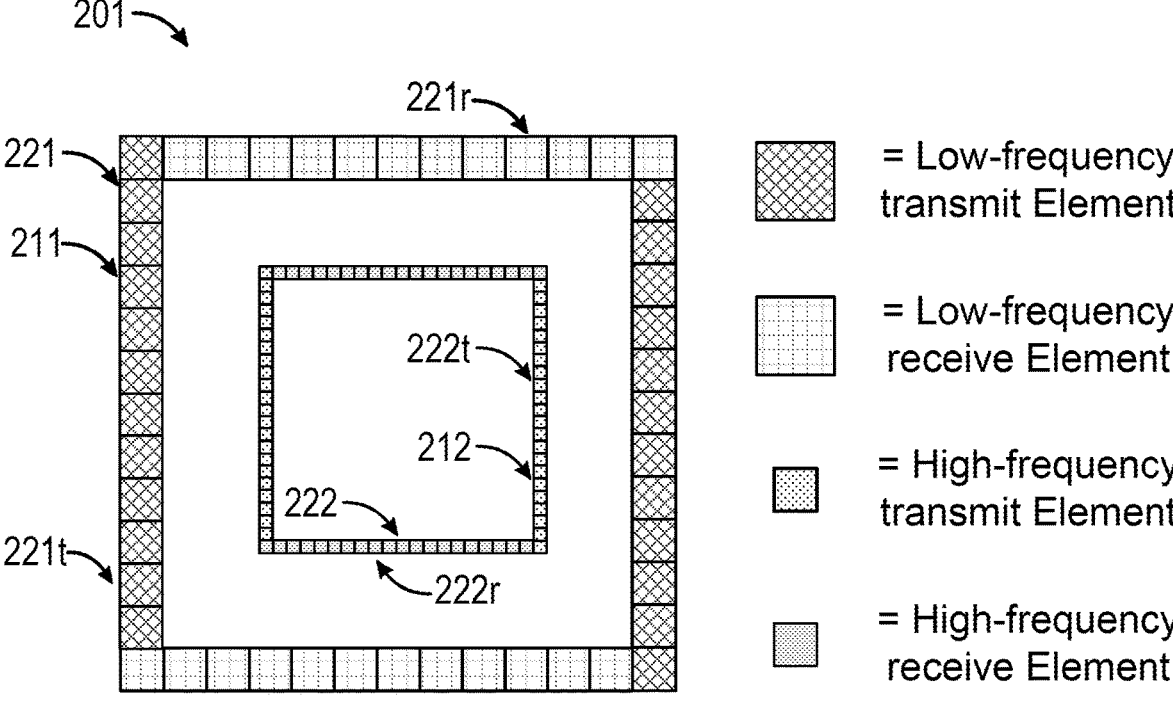

In a further example embodiment, and with reference to FIGS. 2A-2C, a transducer 201, similar to transducer 101, is disclosed. In an example embodiment, the transducer 201 is a rectangular boundary array ("RBA") transducer. The transducer 201, in an example embodiment, may comprise a first rectangular boundary array 211 of a first plurality of ultrasonic transducers 221 and a second rectangular boundary array 212 of a second plurality of ultrasonic transducers 222. In an example embodiment, the second rectangular boundary array 212 is positioned within the first rectangular boundary array 211.

Although described herein as a rectangular shape, the RBA transducer shapes can be square, triangular, octagonal, hexagonal, rectilinear, and or any suitable shape. FIG. 2A illustrates a 4×4 RBA embedded in a 16×16 RBA, however any suitable number of elements may be used in a nested pair of RBA's. In accordance with various example embodiments, although described herein as just two RBA's one nested inside the other, in other example embodiments, the RBA transducer may comprise three or more RBA's successively nested. In an example embodiment, the RBA's are concentric.

In an example embodiment, the first plurality of ultrasonic transducers 221 include a first set of transmitting elements 221$t$ and a first set of receiving elements 221$r$, and the second plurality of ultrasonic transducers 222 include a second set of transmitting elements 222$t$ and a second set of receiving elements 222$r$. In an example embodiment, the first set of transmitting elements 221$t$, the first set of receiving elements 221$r$, the second set of transmitting elements 222$t$ and the second set of receiving elements 222$r$ are controlled independently. In an example embodiment, the transmit/receive elements are typically rectangular in cross section, though any suitable shape may be used. The size of each element can be any size suitable for the intended application/frequency, etc. In an example embodiment, each element may comprise the piezo electric material and/or the acoustic stack. Moreover, each element may be any suitable structure for converting between energy and acoustic wave signals such as capacitive micromachined ultrasonic transducers (cMUTs) or piezoelectric micromachined ultrasonic transducers (pMUTS).

In an example embodiment, the controller 130 is configured to control transmit beamformer 131 to cause it transmit at least one of a first signal having a first frequency using the first set of transmitting elements 221*t* at an object or a second signal having a second frequency using the second set of transmitting elements 222*t* at the object. In an example embodiment, the controller 130 is configured to control receive beamformer 132 to cause it to receive the at least one of the first signal using the first set of receiving elements or the second signal using the second set of receiving elements.

In a further example embodiment, the imaging system 100 further comprises: a memory 180 configured to store a reconstructed image; and a display 150 configured to render the reconstructed image.

In an example embodiment, the controller 130 is configured to control the relevant components (such as the receive beamformer 132 and scan converter 140) to: reconstruct the image based on the received first signal or the received second signal, and render, on the display 150, the reconstructed image.

In an example embodiment, in order to transmit the at least one of the first signal or the second signal, the controller 130 is configured to transmit the first signal using the first set of transmitting elements 221*t* and the second signal using the second set of transmitting elements 222*t*, and in order to receive the at least one of the first signal or the second signal the controller is configured to receive the first signal using the first set of receiving elements 221*r* and the second signal using the second set of receiving elements 222*r*. As used herein, the "set" of transmitting or receiving elements, may refer to all of the elements of that type (e.g., transmit elements in the inner RBA, or a subset thereof). Moreover, in an example embodiment, the set may mean a pair of linear arrays of similar elements positioned opposite each other. In an example embodiment, the second frequency is at a higher frequency than the first frequency. In an example embodiment, the second RBA is an inner RBA and the first RBA is an outer RBA. Stated another way, in an example embodiment, the imaging system (and/or the RBA's themselves) is configured such that the inner RBA transmits and/or receives at a higher frequency than the outer RBA. In an example embodiment, the controller 130 is further configured to control the receive beamformer 132, scan converter 140, etc., to reconstruct a composite image based on the received first signal and the received second signal. In an example embodiment, and with brief reference to FIG. 3, the array elements from a column or row are electrically bussed together to a single transmit/receive channel to increase SNR while also eliminating the need for additional transmit/receive channels. However any suitable number of channels may be used per array of elements. Stated another way, a channel may comprise any suitable number of elements.

In an example embodiment, the controller 130 is configured to determine whether to transmit the first signal using the first set of transmitting elements 221*t* or the second signal using the second set of transmitting elements 222*t* based on user input. In this example embodiment, the user input indicates at least one of a location of an object to image, a desired transmit/receive frequency, and a desired amount of penetration or one of the first transmitting elements or the second transmitting elements to transmit. In an example embodiment, the user input may select among post processing modes including: time gain control, spatial and frequency compounding, elastography, tissue harmonic imaging, and contrast imaging among others.

In an example embodiment, the imaging system further comprises a silicon substrate or other integrated circuit. In an example embodiment, the first rectangular boundary array and the second rectangular boundary array are positioned within the silicon substrate. In an example embodiment, the imaging system 100 further comprises a plurality of interconnections. For example, the plurality of interconnections may comprise a first set of interconnections and a second set of interconnections. In this example embodiment, the first set of interconnections may be configured to interconnect the first plurality of ultrasonic transducers and the second set of interconnections may be configured to interconnect the second plurality of ultrasonic transducers.

In other example embodiments, the RBA transducer 101/201 may be configured to transmit using the two outer columns (221*t*) and to receive using the two inner rows (222*r*). Conversely, the RBA transducer 101/201 may be configured to transmit using the two inner columns (222*t*) and to receive using the two outer rows (221*r*). Thus, although described herein in some embodiments as the controller selecting between the inner and outer elements for transmit/receive communications, in other embodiments, the transmission and reception can occur with one on the inner elements and one on the outer elements.

Moreover, although in certain examples (consistent with some of the figures herein) the transmit elements are illustrated as being in columns and the receive elements are illustrated as being in rows, the application is not so limited. The transmit elements can be in rows and the receive elements can be in columns, or any suitable orientations. In an example embodiment the first boundary array is arranged in a rectangular array, a hexagonal array, a circular array or other polygonal shaped array, and the second boundary array is arranged in a rectangular array, a hexagonal array, a circular array or other polygonal shaped array. In an example embodiment, the second plurality of ultrasonic transducers has less ultrasonic transducers than the first plurality of ultrasonic transducers.

Figure 3:
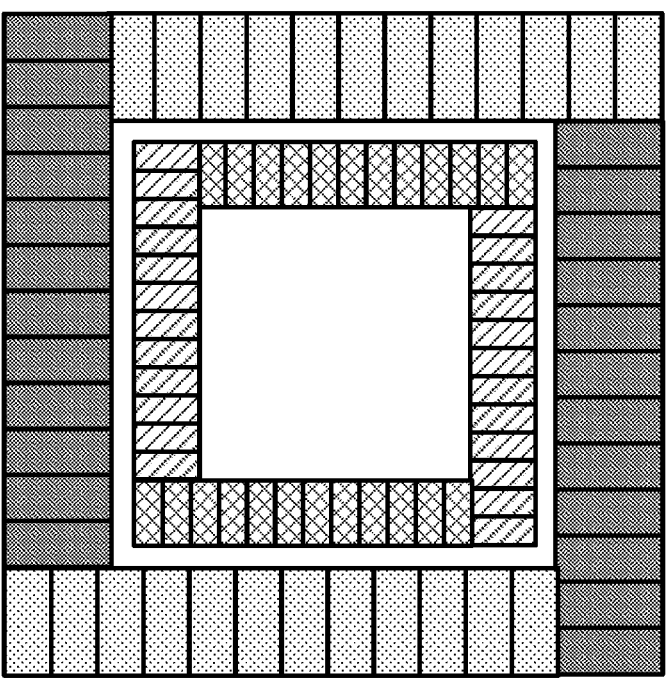
FIG. 3 is another example block diagram of a rectangular boundary array transducer in accordance with an example embodiment.
Figure 3:
Figure 3:
Figure 3:
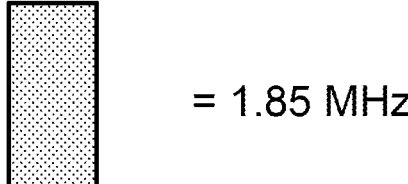

With momentary reference to FIG. 3, in one example embodiment, the outer RBA transmitting elements may be configured to transmit at 1.20 MHz, the outer RBA receiving elements may be configured to receive at 1.85 MHz, the inner RBA transmitting elements may be configured to transmit at 2.5 MHz, and the inner RBA receiving elements may be configured to receive at 3.85 MHz. However, the elements may be configured to transmit and receive at any suitable frequencies. It is noted that regardless of the chosen frequencies, the inner frequencies may, in an example embodiment, both be higher than the outer frequencies. The embodiment shown in FIG. 3 comprises four 1-D arrays for each RBA of the two RBA's. However any suitable number of 1-D arrays may form each RBA.

In an example embodiment, the inner rectangular boundary array is configured to scan an area closer to a surface of the second plurality of ultrasonic transducers than the outer rectangular boundary array. In an example embodiment, the inner rectangular boundary array operates at a higher frequency than the outer rectangular boundary array. This can, for example result in finer spatial resolution but less penetration than what is provided by the outer rectangular boundary array.

In an example embodiment, the first and second rectangular boundary arrays are configured to provide whole body imaging including imaging of different portions of a subject that requires different amounts of penetration. In an example embodiment, the first and second rectangular boundary arrays are configured to be used in connection with tissue harmonic imaging and/or dual-frequency imaging. Due to the nonlinear oscillations, higher harmonics will be generated, which can be received by the higher-frequency portions of the multi-RBA. In an example embodiment, the first and second rectangular boundary arrays are configured to allow for super-resolution imaging where microbubbles are injected into the bloodstream as above, but further signal processing allows visualization and imaging of individual bubbles over time. Thus, the imaging system may be configured to allow transmitting a signal at a first frequency and receiving a signal at a second frequency that is different than the first frequency.

In an example embodiment, the first plurality of ultrasonic transducers and the second plurality of ultrasonic transducers transmit at approximately 1-4 MHz to excite microbubbles within a bloodstream of a patient.

With reference now to FIG. 4, in accordance with an example embodiment, a method 400 for image reconstruction is disclosed comprising determining (410), by a processor, whether to deliver energy to a first rectangular boundary array of a first plurality of ultrasonic transducers, or a second rectangular boundary array of a second plurality of ultrasonic transducers, the second rectangular boundary array being positioned within the first rectangular boundary array. The method 400 may further comprise: determining (420), by the processor, an amount of energy to be delivered to the first plurality of ultrasonic transducers or the second plurality of ultrasonic transducers; and delivering (430), by the processor, the amount of energy to the first plurality of ultrasonic transducers or the second plurality of ultrasonic transducers. In an example embodiment, the first plurality of ultrasonic transducers has a first transmitting element and a first receiving element. In an example embodiment, the method 400 further comprises: transmitting (440) at least one of a first signal having a first frequency using the first transmitting element at an object or a second signal having a second frequency using the second transmitting element; and receiving (450) the at least one of the first signal using the first receiving element or the second signal using the second receiving element. In an example embodiment, the method 400 further comprises: reconstructing (460) an image based on the received first signal or the received second signal, and rendering (470), on a display, the reconstructed image. In an example embodiment, the image is reconstructed based on the received first signal or the received second signal by reconstructing the image based on the received first signal and the received second signal to form a composite image.

With reference now back to FIG. 1, the term "computer-readable medium" is used to define any medium that can store and provide instructions and other data to a processor, particularly where the instructions are to be executed by a processor and/or other peripheral of the processing system. Such medium can include non-volatile storage, volatile storage and transmission media. Non-volatile storage may be embodied on media such as optical or magnetic disks. Storage may be provided locally and in physical proximity to a processor or remotely, typically by use of network connection. Non-volatile storage may be removable from computing system, as in storage or memory cards or sticks that can be easily connected or disconnected from a computer using a standard interface.

The computing system may include a user interface 160. The user interface 160 may include an input/output device. The input/output device may receive user input, such as a user interface element, hand-held controller that provides tactile/proprioceptive feedback, a button, a dial, a microphone, a keyboard, or a touch screen, and/or provides output, such as a display, a speaker, an audio and/or visual indicator, or a refreshable braille display. The display 150 may be a computer display, a tablet display, a mobile phone display, an augmented reality display or a virtual reality headset. The display 150 may output or provide a virtual environment that mimics actions of the patient and/or provide information regarding the neural activity of the patient or other information.

The user interface 160 may include an input/output device that receives user input, such as a user interface element, a button, a dial, a microphone, a keyboard, or a touch screen, and/or provides output, such as a display, a speaker, headphones, an audio and/or visual indicator, a device that provides tactile/proprioceptive feedback or a refreshable braille display. The speaker may be used to output audio associated with the audio conference and/or the video conference. The user interface 160 may receive user input that may include configuration settings for one or more user preferences, such as a selection of joining an audio conference or a video conference when both options are available, for example.

The computing system may have a network that couples a server with the computing device. The network may be a local area network (LAN), a wide area network (WAN), a cellular network, the Internet, or combination thereof, that connects, couples and/or otherwise communicates between the various components of the system with the server. The server may be a remote computing device or system that includes a memory, a processor and/or a network access device coupled together via a bus. The server may be a computer in a network that is used to provide services, such as accessing files or sharing peripherals, to other computers in the network.

The computing system may include a communication interface, such as a network access device. The communication interface may include a communication port or channel, such as one or more of a Dedicated Short-Range Communication (DSRC) unit, a Wi-Fi unit, a Bluetooth® unit, a radio frequency identification (RFID) tag or reader, or a cellular network unit for accessing a cellular network (such as 3G, 4G or 5G). The communication interface may transmit data to and receive data among the different components.

The server may include a database. A database is any collection of pieces of information that is organized for search and retrieval, such as by a computer, and the database may be organized in tables, schemas, queries, reports, or any other data structures. A database may use any number of database management systems. The information may include real-time information, periodically updated information, or user-inputted information.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program product and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware so as to perform the functions described herein will be apparent to persons skilled in the relevant art(s).

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an Internet-based embodiment, an entirely hardware embodiment, or an embodiment combining aspects of the Internet, software, and hardware. Furthermore, the system may take the form of a computer program product on a computer-readable storage medium having computer-readable program code means embodied in the storage medium. Any suitable computer-readable storage medium may be utilized, including hard disks, CD-ROM, BLU-RAY DISC®, optical storage devices, magnetic storage devices, and/or the like.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. An imaging system, comprising:
    a first rectangular boundary array being arranged in the shape of a rectangle, the first rectangular boundary array having two outer columns each including at least two adjacent independently controlled ultrasonic transducers and being opposite to one another and two outer rows each including at least two adjacent independently controlled ultrasonic transducers and being opposite to one another, the at least two adjacent independently controlled ultrasonic transducers on each of the two outer columns being transmit elements and the at least two adjacent independently controlled ultrasonic transducers on each of the two outer rows being receive elements;

a second rectangular boundary array being arranged in the shape of a rectangle and positioned within the first rectangular boundary array, the second rectangular boundary array having two inner columns each including at least two adjacent independently controlled ultrasonic transducers and being opposite to one another and two inner rows each including at least two adjacent independently controlled ultrasonic transducers and being opposite to one another, the at least two adjacent independently controlled ultrasonic transducers on each of the two inner columns being transmit elements and the at least two adjacent independently controlled ultrasonic transducers on each of the two inner rows being receive elements; and a controller coupled to the transmit elements of the two outer columns and the two inner columns and to the receive elements of the two outer rows and the two inner rows and configured to:

control an amount of energy delivered to the transmit elements.

2. The imaging system of claim 1, further comprising:
a transmit beamformer coupled to the transmit elements and configured to:
deliver the energy to independently control and excite the transmit elements.

3. The imaging system of claim 1, wherein the controller is further configured to:
transmit at least one of a first signal having a first frequency using the transmit elements of the two outer columns at an object or a second signal having a second frequency using the transmit elements of the two inner columns at the object; and
receive the at least one of the first signal using the receive elements of the two outer rows or the second signal using the receive elements of the two inner rows.

4. The imaging system of claim 3, further comprising:
a memory configured to store a reconstructed image; and
a display configured to render the reconstructed image;
wherein the controller is further configured to:
reconstruct the image based on the received first signal or the received second signal, and
render, on the display, the reconstructed image.

5. The imaging system of claim 3, wherein to transmit the at least one of the first signal or the second signal the controller is configured to transmit the first signal using the transmit elements of the two outer columns and the second signal using the transmit elements of the two inner columns, wherein to receive the at least one of the first signal or the second signal the controller is configured to receive the first signal using the receive elements of the two outer rows and the second signal using the receive elements of the two inner rows, wherein the second frequency is at a higher frequency than the first frequency, wherein the controller is further configured to reconstruct a composite image based on the received first signal and the received second signal.

6. The imaging system of claim 3, wherein the controller is configured to determine whether to transmit the first signal using the transmit elements of the two outer columns or the second signal using the transmit elements of the two inner columns based on user input, wherein the user input indicates at least one of a location of an object to image, a desired transmit/receive frequency, a desired amount of penetration or one of the transmit elements of the two outer columns or the transmit elements of the two inner columns to transmit.

7. The imaging system of claim 1, further comprising:
a silicon substrate; and
a plurality of interconnections;
wherein the first rectangular boundary array and the second rectangular boundary array are positioned within the silicon substrate, wherein a first set of the plurality of interconnections interconnect the at least two adjacent independently controlled ultrasonic transducers on each of the two outer columns and a second set of plurality of interconnections interconnect the at least two adjacent independently controlled ultrasonic transducers on each of the two inner columns.

8. The imaging system of claim 1, wherein the second rectangular boundary array is an inner rectangular boundary array and the first rectangular boundary array is an outer rectangular boundary array.

9. The imaging system of claim 8, wherein the inner rectangular boundary array is configured to scan an area closer to a surface than the outer rectangular boundary array, wherein the inner rectangular boundary array operates at a higher frequency than the outer rectangular boundary array, which results in finer spatial resolution but less penetration than the outer rectangular boundary array.

10. The imaging system of claim 1, wherein the first and second rectangular boundary arrays are configured to provide whole body imaging including imaging of different portions of a subject that requires different amounts of penetration and allow for dual-frequency imaging and super-resolution imaging including allowing transmitting a signal at a first frequency and receiving a signal at a second frequency that is different than the first frequency, wherein the at least two adjacent independently controlled ultrasonic transducers on each of the two outer columns and the at least two adjacent independently controlled ultrasonic transducers on each of the two inner columns transmit at approximately 1-4 MHz to excite microbubbles within a bloodstream of a patient.

11. The imaging system of claim 1, wherein the at least two adjacent independently controlled ultrasonic transducers on each of the two inner columns are configured to transmit at a frequency of about 2.5 MHz and the at least two adjacent independently controlled ultrasonic transducers on each of the two outer columns are configured to transmit at a frequency of about 1.2 MHz.

* * * * *